United States Patent
Facchetti et al.

(10) Patent No.: US 9,147,850 B2
(45) Date of Patent: Sep. 29, 2015

(54) PERYLENE-BASED SEMICONDUCTORS AND METHODS OF PREPARATION AND USE THEREOF

(75) Inventors: Antonio Facchetti, Chicago, IL (US); Zhihua Chen, Skokie, IL (US); He Yan, Kowloon (HK); Marcel Kastler, Mannheim (DE); Florian Doetz, Singapore (SG)

(73) Assignees: BASF SE, Ludwigshafen (DE); Polyera Corporation, Skokie, IL (US)

( * ) Notice: Subject to any disclaimer, the term of this patent is extended or adjusted under 35 U.S.C. 154(b) by 52 days.

(21) Appl. No.: 13/995,733

(22) PCT Filed: Dec. 19, 2011

(86) PCT No.: PCT/IB2011/055760
§ 371 (c)(1),
(2), (4) Date: Jun. 19, 2013

(87) PCT Pub. No.: WO2012/090110
PCT Pub. Date: Jul. 5, 2012

(65) Prior Publication Data
US 2013/0270543 A1    Oct. 17, 2013

Related U.S. Application Data

(60) Provisional application No. 61/428,668, filed on Dec. 30, 2010.

(51) Int. Cl.
*H01L 29/08* (2006.01)
*H01L 51/00* (2006.01)
*C07D 471/06* (2006.01)
*H01L 51/05* (2006.01)

(52) U.S. Cl.
CPC .......... *H01L 51/0072* (2013.01); *C07D 471/06* (2013.01); *H01L 51/0053* (2013.01); *H01L 51/0541* (2013.01); *H01L 51/0545* (2013.01)

(58) Field of Classification Search
CPC ................... H01L 51/0072; H01L 51/0053
USPC .......................................................... 257/40
See application file for complete search history.

(56) References Cited

U.S. PATENT DOCUMENTS

| | | | |
|---|---|---|---|
| 7,605,394 B2 | 10/2009 | Marks et al. | |
| 7,678,463 B2 | 3/2010 | Marks et al. | |
| 7,893,265 B2 | 2/2011 | Facchetti et al. | |
| 7,902,363 B2 | 3/2011 | Facchetti et al. | |
| 2010/0319778 A1 | 12/2010 | Kastler et al. | |
| 2013/0112964 A1 | 5/2013 | Koehler et al. | |

FOREIGN PATENT DOCUMENTS

| | | |
|---|---|---|
| WO | 2008 063609 | 5/2008 |
| WO | 2008 085942 | 7/2008 |
| WO | 2009 098252 | 8/2009 |

OTHER PUBLICATIONS

International Search Report Issued May 31, 2012 in PCT/IB11/55760 Filed Dec. 19, 2011.

*Primary Examiner* — Douglas Menz
(74) *Attorney, Agent, or Firm* — Oblon, McClelland, Maier & Neustadt, L.L.P.

(57) ABSTRACT

Provided are semiconductors prepared from an enantiomerically enriched mixture of a nitrogen-functionalized rylene bis(dicarboximide) compound. Specifically, the enantiomerically enriched mixture has unexpected electron-transport efficiency compared to the racemate or either of the enantiomers in optically pure form.

20 Claims, 2 Drawing Sheets a)

b)

c)

d)

PERYLENE-BASED SEMICONDUCTORS AND METHODS OF PREPARATION AND USE THEREOF

CROSS REFERENCE TO RELATED APPLICATIONS

The present application is a 35 U.S.C. §371 national stage patent application of International patent application PCT/IB2011/055760, filed on Dec. 19, 2011, published as WO/2012/090110 on Jul. 5, 2012, the text of which is incorporated by reference, and claims the benefit of the filing date of U.S. provisional application No. 61/428,668, filed on Dec. 30, 2010, the text of which is also incorporated by reference.

BACKGROUND

Recent developments in organic-based light-emitting diodes (OLEDs), photovoltaics (OPVs), and field-effect transistors (OFETs) have opened up many opportunities in the field of organic electronics. One of the challenges in this field is to develop thin film devices that have environmentally stable electron-transporting (n-type) organic semiconductors with high-mobility. The performance and stability of organic n-type materials have significantly lagged behind their p-type counterparts. Some challenges for advancing the technology of organic n-type materials include their vulnerability to ambient conditions (e.g., air) and solution-processability. For example, it is desirable for these materials to be soluble in common solvents so that they can be formulated into inks for inexpensive printing processes.

The most common air-stable n-type organic semiconductors include perfluorinated copper phthalocyanine ($CuF_{16}Pc$), fluoroacyl oligothiophenes (e.g., DFCO-4TCO), N,N'-fluorocarbon-substituted naphthalene diimides (e.g., NDI-F, NDI-XF), cyano-substituted perylene bis(dicarboximide)s (e.g., $PDI-FCN_2$), and cyano-substituted naphthalene bis(dicarboximide)s (e.g., $NDI-8CN_2$). See, e.g., Bao et al. (1998), J. Am. Chem. Soc., 120: 207-208; de Oteyza et al. (2005), Appl. Phys. Lett., 87: 183504; Schon et al. (2000), Adv Mater. 12: 1539-1542; Ye et al. (2005), Appl. Phys. Lett., 86: 253505; Yoon et al. (2006), J. Am. Chem. Soc., 128: 12851-12869; Tong et al. (2006), J. Phys. Chem. B., 110: 17406-17413; Yuan et al. (2004), Thin Solid Films, 450: 316-319; Yoon et al. (2005), J. Am. Chem. Soc., 127: 1348-1349; Katz et al. (2000), J. Am. Chem. Soc., 122: 7787-7792; Katz et al. (2000), Nature (London), 404: 478-481; Katz et al (2001), Chem. Phys. Chem., 3: 167-172; Jung et al. (2006), Appl. Phys. Lett., 88: 183102; Yoo et al. (2006), IEEE Electron Device Lett., 27: 737-739; Jones et al. (2004), Angew. Chem., Int. Ed. Engl., 43: 6363-6366; and Jones et al. (2007), J. Am. Chem. Soc., 129: 15259-15278. Rylene bis(dicarboximide)s are particularly attractive because of their robust nature, flexible molecular orbital energetics, and excellent charge transport properties. However, high-mobility rylene compounds, including $PDI-FCN_2$ and NDI-F, have poor solubility. Soluble rylene compounds, on the other hand, usually have poor charge transport properties.

Accordingly, given potential applications in inexpensive and large-area organic electronics that can be produced by high-throughput reel-to-reel manufacture, the art desires new organic semiconductor materials, especially those possessing desirable properties such as air stability, high charge transport efficiency, and good solubility in common solvents.

SUMMARY

In light of the foregoing, the present teachings provide organic semiconductors and related compositions, composites, and/or devices that can address various deficiencies and shortcomings of the state-of-the-art, including those outlined above.

More specifically, the present teachings provide organic semiconductors prepared from an enantiomerically enriched mixture of a nitrogen-functionalized rylene bis(dicarboximide) compound. In particular, the substituent of each of the two imide nitrogen atoms of the compound includes a stereogenic center and has either an (R)- or an (S)-configuration. It was surprisingly found that an enantiomerically enriched mixture in which the ratio of the (R,R)-stereoisomers to the (S,S)-stereoisomers (or vice versa) is between about 0.8:0.2 and about 0.98:0.02 can lead to highly improved electronic properties when compared to a 1:1 (or racemic) mixture of the (R,R)- and (S,S)-stereoisomers. Specifically, when incorporated as the semiconductor in a thin film transistor, the enantiomerically enriched mixture of the present teachings can exhibit a mobility that is at least two times and in some cases, as much as six times higher than a racemic mixture of the same compound. In addition, it was surprisingly found that the enantiomerically enriched mixture of the present teachings has substantially similar, and in some cases, better electronic properties compared to either of the optically pure isomers.

The foregoing as well as other features and advantages of the present teachings will be more fully understood from the following figures, description, and claims.

BRIEF DESCRIPTION OF THE DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
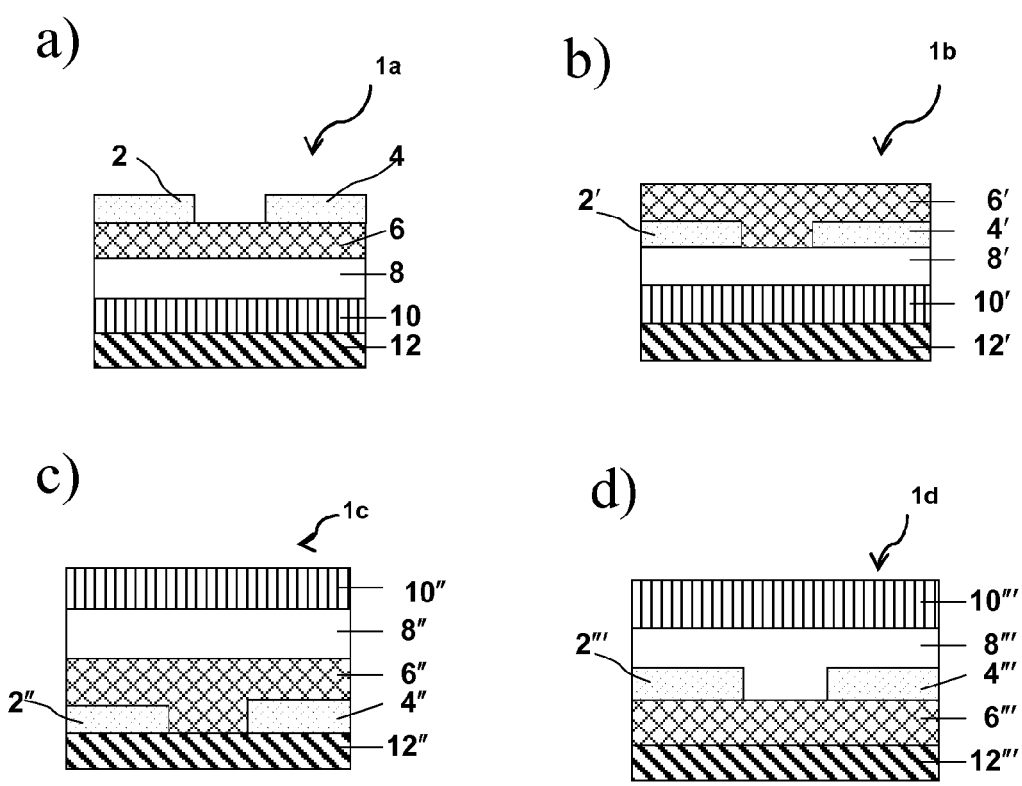
FIG. 1 illustrates four different configurations of thin film transistors: bottom-gate top contact (top left), bottom-gate bottom-contact (top right), top-gate bottom-contact (bottom left), and top-gate top-contact (bottom right); each of which can be used to incorporate polymers of the present teachings.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm$^2$/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm$^2$/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, "halo" or "halogen" refers to fluoro, chloro, bromo, and iodo.

As used herein, "oxo" refers to a double-bonded oxygen (i.e., $=$O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neo-pentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group (which, in some cases, can be expressed as —S(O)$_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and optionally can be substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which optionally can be substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which optionally can be substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

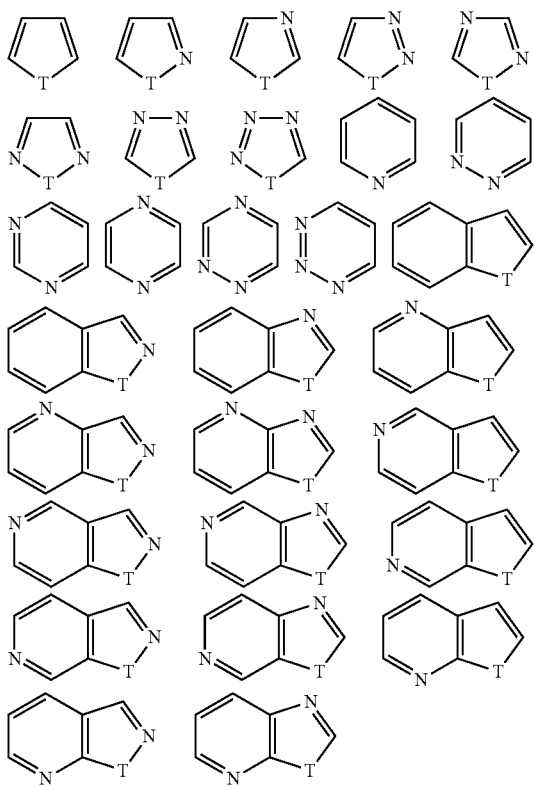

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, "arylalkyl" refers to an -alkyl-aryl group, where the arylalkyl group is covalently linked to the defined chemical structure via the alkyl group. An arylalkyl group is within the definition of a —Y—C$_{6-14}$ aryl group, where Y is as defined herein. An example of an arylalkyl group is a benzyl group (—CH$_2$—C$_6$H$_5$). An arylalkyl group optionally can be substituted, i.e., the aryl group and/or the alkyl group, can be substituted as disclosed herein.

Compounds of the present teachings can include a "divalent group" defined herein as a linking group capable of forming a covalent bond with two other moieties. For example, compounds of the present teachings can include a divalent C$_{1-20}$ alkyl group (e.g., a methylene group), a divalent C$_{2-20}$ alkenyl group (e.g., a vinylyl group), a divalent C$_{2-20}$ alkynyl group (e.g., an ethynylyl group). a divalent C$_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

As used herein, a "solubilizing group" refers to a functional group that makes the resultant molecule more soluble in at least one common organic solvent than a hydrogen atom would if it occupied the same position in a molecule (for the same molecule-solvent combination). Examples of solubilizing groups include alkyl groups (e.g., methyl, ethyl, iso-propyl, n-propyl, iso-butyl, sec-butyl, n-butyl, tert-butyl, n-pentyl, iso-pentyl, neo-pentyl, hexyl, 20methyl hexyl, octyl, 3,7-dimethyl octyl, decyl, deodecyl, tetradecyl, hexadecyl), alkoxy groups (e.g., methoxy, ethoxy, iso-propoxy, n-propoxy, iso-butyloxy, sec-butyloxy, n-butyloxy, hexyloxy, 2-methyl hexyloxy, octyloxy, 3,7-dimethyl octyloxy, decyloxy, dodecyloxy, tetradecyloxy, hexadecyloxy), thioalkyl groups (e.g., thiooctyl), alkyethers, and thioethers.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide (N3), thiocyanate (SCN), nitro (NO$_2$), cyanate (CN), water (H$_2$O), ammonia (NH$_3$), and sulfonate groups (e.g., OSO$_2$—R, wherein R can be a C$_{1-10}$ alkyl group or a C$_{6-14}$ aryl group each optionally substituted with 1-4 groups independently selected from a C$_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "cyanating agent" can be LiCN, NaCN, KCN, CuCN, AgCN, trimethylsilyl cyanide (TMSCN), or any other cyanating agent known by those skilled in the art.

The electron-donating or electron-withdrawing properties of several hundred of the most common substituents, reflecting all common classes of substituents have been determined, quantified, and published. The most common quantification of electron-donating and electron-withdrawing properties is in terms of Hammett G values. Hydrogen has a Hammett G value of zero, while other substituents have Hammett G values that increase positively or negatively in direct relation to their electron-withdrawing or electron-donating characteristics. Substituents with negative Hammett G values are considered electron-donating, while those with positive Hammett G values are considered electron-withdrawing. See Lange's Handbook of Chemistry, 12th ed., McGraw Hill, 1979, Table 3-12, pp. 3-134 to 3-138, which lists Hammett G values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —NO$_2$, —CN, —NC, —S(R$^0$)$_2^+$, —N(R$^0$)$_3^+$, —SO$_3$H, —SO$_2$R$^0$, —SO$_3$R$^0$, —SO$_2$NHR$^0$, —SO$_2$N(R$^0$)$_2$, —COOH, —COR$^0$, —COOR$^0$, —CONHR$^0$, —CON(R$^0$)$_2$, C$_{1-40}$ haloalkyl groups, C$_{6-14}$ aryl groups, and 5-14 membered electron-poor heteroaryl groups; where R$^0$ is a C$_{1-20}$ alkyl group, a C$_{2-20}$ alkenyl group, a C$_{2-20}$ alkynyl group, a C$_{1-20}$ haloalkyl group, a C$_{1-20}$ alkoxy group, a C$_{6-14}$ aryl group, a C$_{3-14}$ cycloalkyl group, a 3-14 membered cycloheteroalkyl group, and a 5-14 membered heteroaryl group, each of which optionally can be substituted as described herein. For example, each of the C$_{1-20}$ alkyl group, the C$_{2-20}$ alkenyl group, the C$_{2-20}$ alkynyl group, the C$_{1-20}$ haloalkyl group, the C$_{1-20}$ alkoxy group, the C$_{6-14}$ aryl group, the C$_{3-14}$ cycloalkyl group, the 3-14 membered cycloheteroalkyl group, and the 5-14 membered heteroaryl group optionally can be substituted with 1-5 small electron-withdrawing groups such as F, Cl, Br, —NO$_2$, —CN, —NC, —S(R$^o$)$_2{}^+$, —N(R$^o$)$_3{}^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, and —CON(R$^o$)$_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —OR$^o$, —NH$_2$, —NHR$^o$, —N(R$^o$)$_2$, and 5-14 membered electron-rich heteroaryl groups, where R$^o$ is a C$_{1-20}$ alkyl group, a C$_{2-20}$ alkenyl group, a C$_{2-20}$ alkynyl group, a C$_{6-14}$ aryl group, or a C$_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., Heterocyclic Chemistry (John Wiley & Sons, New York, 1960).

At various places in the present specification, substituents are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Throughout the specification, structures may or may not be presented with chemical names. Where any question arises as to nomenclature, the structure prevails.

Generally, the present teachings relate to a thin film semiconductor comprising an enantiomerically enriched mixture of a compound of formula I:

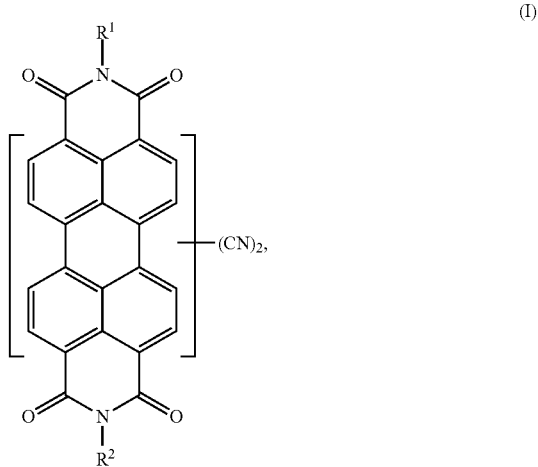

where R$^1$ and R$^2$ are compositionally identical or substantially identical branched organic groups that include a stereogenic center. While formula I is intended to include various possible regioisomers, it is intended that formula I encompasses, at a minimum, the isomers:

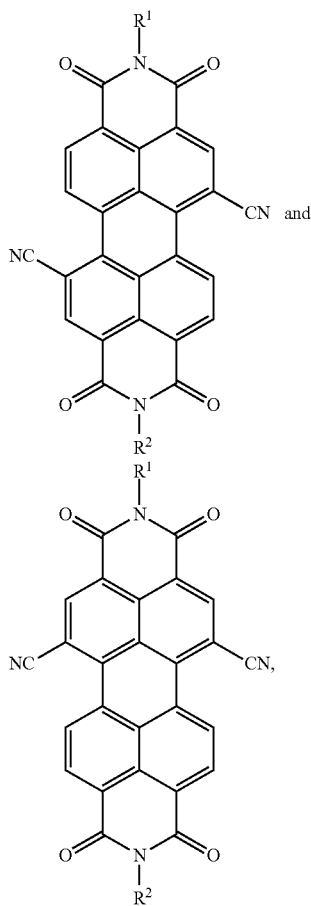

which are known to be the most kinetically stable among the various possible regioisomers of formula I.

More specifically, in certain embodiments, $R^1$ and $R^2$ can be identical and selected from a branched $C_{4-40}$ alkyl group, a branched $C_{4-40}$ alkenyl group and a branched $C_{4-40}$ haloalkyl group, where the branched $C_{4-40}$ alkyl group, the branched $C_{4-40}$ alkenyl group, or the branched $C_{4-40}$ haloalkyl group can have a formula selected from:

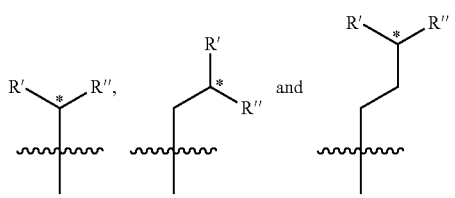

where R' is a $C_{1-20}$ alkyl or haloalkyl group; and R" is different from R' and selected from a $C_{1-20}$ alkyl group, a $C_{2-20}$ alkenyl group, and a $C_{1-20}$ haloalkyl group. The asterisk * denotes a stereogenic center such that $R^1$ and $R^2$ have either an (R)- or an (S)-configuration. The mixture is enantiomerically enriched, that is, the mixture includes an excess of either the (R,R)-stereoisomer (in which both $R^1$ and $R^2$ have the (R)-configuration) or the (S,S)-stereoisomer (in which both $R^1$ and $R^2$ have the (S)-configuration). More specifically, the ratio of (R,R)-stereoisomers:(S,S)-stereoisomers or the ratio of [S,S]-stereoisomers:(R,R)-stereoisomers in the enantiomerically enriched mixture is between about 0.8:0.2 and about 0.98:0.02.

In certain embodiments, $R^1$ and $R^2$ can be substantially identical branched groups that include the same stereogenic center, and independently can be a branched $C_{4-40}$ alkyl group, a branched $C_{4-40}$ alkenyl group, or a branched $C_{4-40}$ haloalkyl group. In embodiments where $R^1$ and $R^2$ are described as being "substantially identical," it is intended to mean that while both $R^1$ and $R^2$ have the same branching pattern including a stereogenic center as represented by one of the formulae:

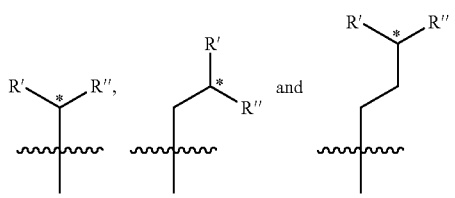

one of R' and R" can be different, for example, in terms of the number of carbon atoms (e.g., a difference of no more than two carbon atoms), the extent of saturation, or substitution with halogen groups. To illustrate, $R^1$ and $R^2$ can be considered substantially identical when both $R^1$ and $R^2$ are a branched group of the formula:

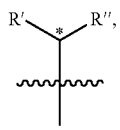

where R' is the same in both $R^1$ and $R^2$, but R" in $R^1$ is different from R" in $R^2$. For example, R" in $R^1$ can be an n-hexyl group, but R" in $R^2$ can be an n-pentyl group, an n-heptyl group, a hexenyl group, or a fluoro-substituted hexyl group (e.g., $(CH_2)_5CF_3$).

In certain embodiments, the enantiomerically enriched mixture can include a pair of enantiomers selected from:

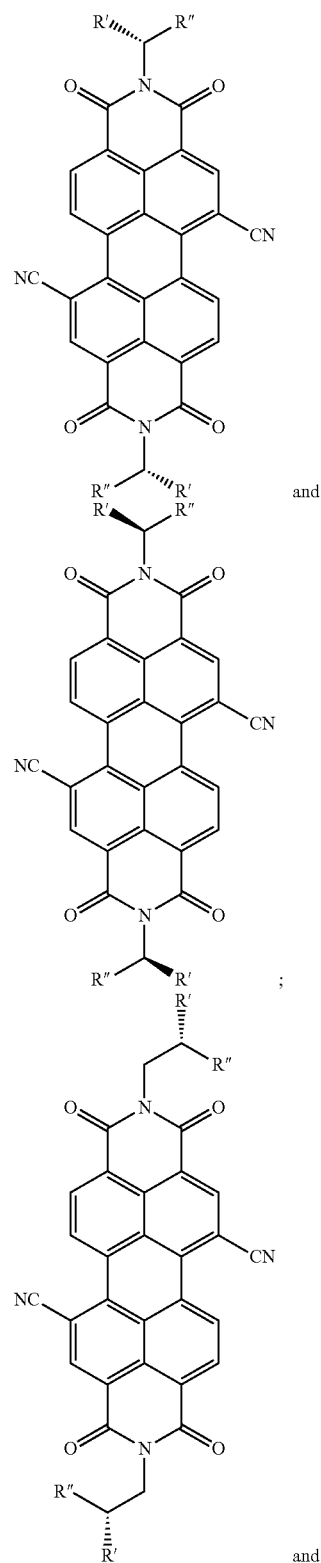

and

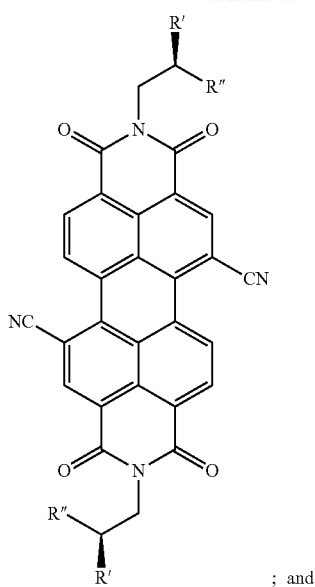

; and

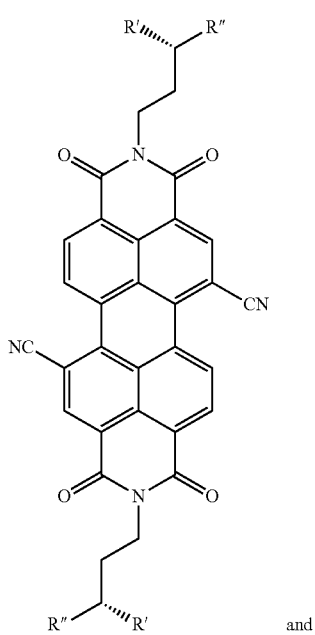

and

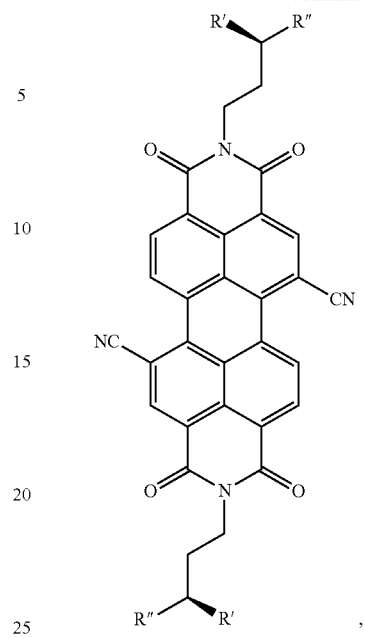

, where R' and R" are as defined herein, and the relative ratio of the two enantiomers in each pair is between about 0.8:0.2 and about 0.98:0.02. In particular embodiments, the relative ratio of the two enantiomers in each pair can be between about 0.90:0.10 and about 0.95:0.05.

In particular embodiments, R' can be a lower alkyl or haloalkyl group having 1 to 6 carbon atoms (e.g., $CH_3$, $CF_3$, $C_2H_5$, $C_2F_5$, $CH_2CF_3$, $C_3H_7$, $C_3F_7$, and $CH_2CH_2CF_3$); while R" is different from R' and has at least 3 carbon atoms. For example, R" can be selected from a $C_{3-20}$ alkyl group, a $C_{3-20}$ alkenyl group, and a $C_{3-20}$ haloalkyl group. In various embodiments, both R' and R" can be linear groups.

To further illustrate, an enantiomerically enriched mixture of the present teachings can include a pair of enantiomers selected from:

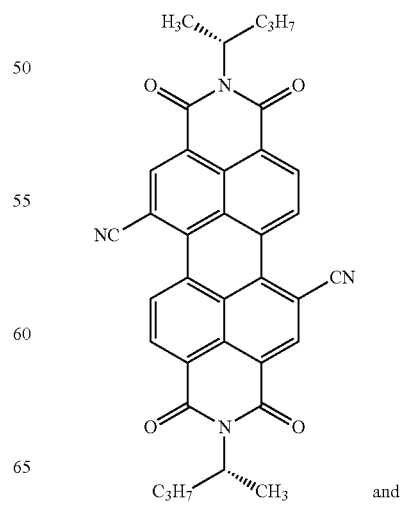

and

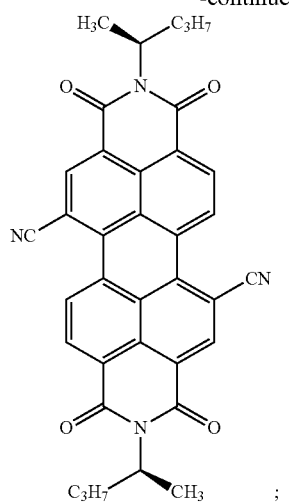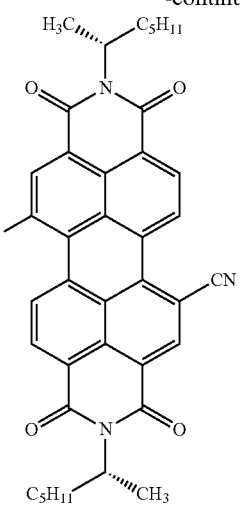 and
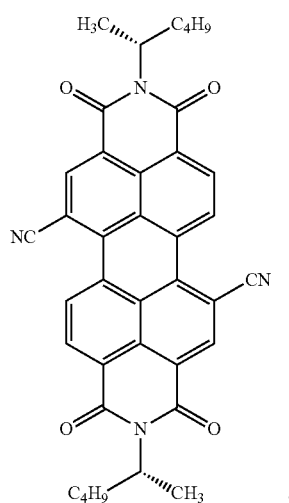 and 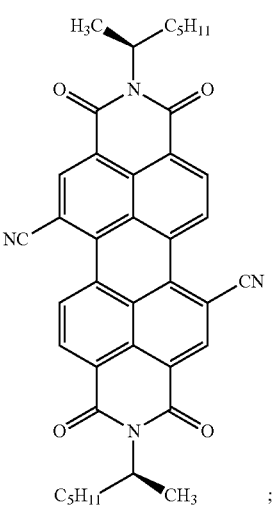;
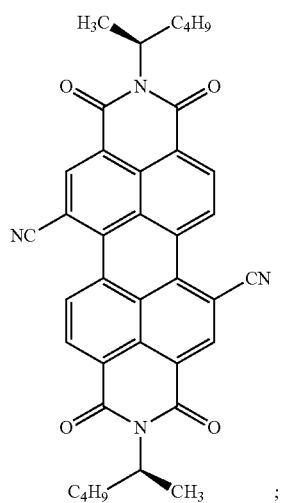; 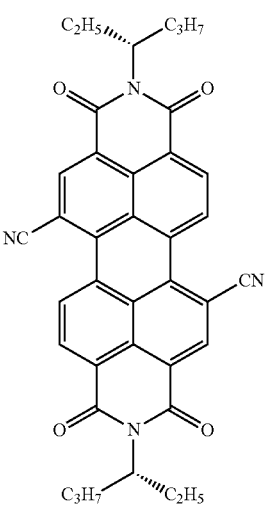 and

-continued

; and

and

, where the relative ratio of the two enantiomers in each pair is between about 0.8:0.2 and about 0.98:0.02. In particular embodiments, the relative ratio of the two enantiomers in each pair can be between about 0.90:0.10 and about 0.95:0.05.

The enantiomerically enriched mixture of the present teachings can be obtained via different methods. A compound of formula I typically can be synthesized by reacting a primary amine with a dianhydride of formula II:

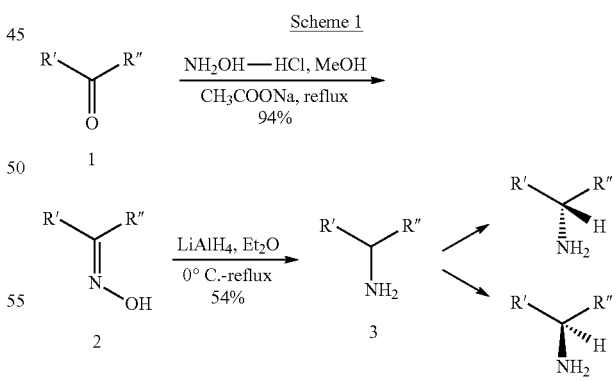

then reacting the resulting bis(dicarboximide) with a cyanating agent to replace the leaving groups (LG) with cyano groups. The primary amine can have a formula selected from:

(IIIa)

$$\underset{NH_2}{R'\diagdown\diagup R''},$$

(IIIb)

$$\underset{NH_2}{\diagup}\underset{}{\diagdown}\underset{}{\overset{R'}{\diagup}}R'', \text{ and}$$

(IIIc)

$$\underset{NH_2}{\diagup}\underset{}{\diagdown}\underset{}{\overset{R'\diagdown\diagup R''}{,}},$$

where R' and R" are as defined herein, and can be prepared in accordance with the procedures outlined in Scheme 1 below.

Scheme 1

$$\underset{O}{\overset{R'\diagdown\diagup R''}{\|}} \xrightarrow[\text{CH}_3\text{COONa, reflux}]{\text{NH}_2\text{OH}-\text{HCl, MeOH}} \underset{94\%}{}$$

1

$$\underset{OH}{\overset{R'\diagdown\diagup R''}{\diagup N\diagdown}} \xrightarrow[\text{0° C.-reflux}]{\text{LiAlH}_4, \text{Et}_2\text{O}} \underset{NH_2}{\overset{R'\diagdown\diagup R''}{}} \nearrow \underset{NH_2}{\overset{R'\diagdown\diagup R''\diagdown H}{}}$$

2    3    $\searrow \underset{NH_2}{\overset{R'\diagdown\diagup R''\diagup H}{}}$ Referring to Scheme 1, ketoxime 2 can be prepared by mixing ketone 1 with hydroxylamine hydrochloride in methanol, followed by addition of sodium acetate, at reflux temperature. To reduce the ketoxime into the amine 3, a solution of ketoxime 2 in diethyl ether can be added dropwise to a suspension of lithium aluminium hydride in dry diethyl ether at 0° C., then heated to reflux for sixteen hours, to provide a racemic mixture of the amine 3.

Various procedures can be used to isolate optically pure enantiomers of amine 3. For example, chiral separation, diastereomeric salt formation, or kinetic resolution can be used. In particular, kinetic resolution of racemates by enzyme-catalyzed acyl transfer reactions can lead to a very high enantiomeric excess (>99.0%). Various enzymes including *Pseudomonas aeruginosa* lipase, subtilisin, and *Candida antarctica* lipase have been studied for their efficiency in kinetic resolution of chiral amines. See, e.g., Davis et al. (2001), Syn. Comm., 31(4): 569-578.

Accordingly, in some embodiments, an enantiomerically enriched mixture of the present teachings can be obtained by using a stereospecific primary amine. For example, an (R,R)-stereoisomer of formula I can be obtained by reacting an (R)-amine with the dianhydride of formula II, which is then combined at the appropriate ratio with the (S,S)-stereoisomer obtained in an analogous manner to provide an enantiomerically enriched mixture of compounds of formula I.

In some embodiments, the present enantiomerically enriched mixture can be prepared from an enantiomerically enriched mixture of the primary amine. While reacting the dianhydride of formula II with an enantiomerically enriched mixture of the primary amine (as opposed to a stereospecific primary amine) will lead to some meso isomers of compounds of formula I, it was found that the presence of the meso isomers has little effect on the semiconducting properties of the enantiomerically enriched mixture as a whole.

In alternative embodiments, the dianhydride of formula II can be reacted with a racemic mixture of the primary amine, which leads to a mixture of the (R,R)-stereoisomer, the (S,S)-stereoisomer, and the achiral meso-(R,S)-stereoisomer. The (R,R)-stereoisomer, and similarly, the (S,S)-stereoisomer, can be isolated using standard separation procedures, and subsequently combined with the other enantiomer at specific ratios to provide the present enantiomerically enriched mixture. Standard separation procedures known to those skilled in the art include, for example, column chromatography, thin-layer chromatography, simulated moving-bed chromatography, and high-performance liquid chromatography, optionally with chiral stationary phases.

The enantiomerically enriched mixture of the present teachings can be used to prepare semiconductor materials (e.g., compositions and composites), which in turn can be used to fabricate various articles of manufacture, structures, and devices. In some embodiments, semiconductor materials incorporating the enantiomerically enriched mixture of the present teachings can exhibit n-type semiconducting activity. It was surprisingly found that an enantiomerically enriched mixture of a compound of formula I according to the present teachings can exhibit highly improved electronic properties when compared to the racemate. Specifically, when incorporated as the semiconductor in a thin film transistor, the enantiomerically enriched mixture of the present teachings exhibits a mobility that can be at least two times and in some cases, as much as six times higher than the racemate. In addition, it was surprisingly found that the enantiomerically enriched mixture of the present teachings has substantially similar, and in some cases, better electronic properties compared to either the (R,R)-stereoisomer or the (S,S)-stereoisomer in substantially pure form (i.e., an optical purity of 99% or greater).

Accordingly, the present teachings provide for electronic devices, optical devices, and optoelectronic devices that include the enantiomerically enriched mixture described herein. Examples of such electronic devices, optical devices, and optoelectronic devices include thin film semiconductors, thin film transistors (e.g., field effect transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators. In some embodiments, the present teachings provide for a thin film semiconductor including the enantiomerically enriched mixture described herein and a field effect transistor device including the thin film semiconductor. In particular, the field effect transistor device has a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material includes an organic dielectric material, an inorganic dielectric material, or a hybrid organic/inorganic dielectric material. In other embodiments, the present teachings provide for photovoltaic devices and organic light emitting devices incorporating a thin film semiconductor that includes the enantiomerically enriched mixture described herein.

Compounds of formula I generally have good solubility in a variety of common solvents. Thus, the present enantiomerically enriched mixture can be processed via inexpensive solution-phase techniques into various electronic devices, optical devices, and optoelectronic devices. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl)ether, diethyl ether, di-isopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that include the enantiomerically enriched mixture disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin coating, drop-casting, zone casting, dip coating, and blade coating.

The present enantiomerically enriched mixture can exhibit versatility in their processing. Formulations including the present enantiomerically enriched mixture can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes the present enantiomerically enriched mixture disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes the enantiomerically enriched mixture disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., PNAS, 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein). The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Accordingly, an aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

FIG. 1 illustrates the four common types of OFET structures: (top left) bottom-gate top-contact structure, (top right) bottom-gate bottom-contact structure, (bottom left) top-gate bottom-contact structure, and (bottom right) top-gate top-contact structure. As shown in FIG. 1, an OFET can include a gate dielectric component (e.g., shown as 8, 8', 8", and 8'''), a semiconductor component or semiconductor layer (e.g., shown as 6, 6', 6", and 6'''), a gate electrode or contact (e.g., shown as 10, 10', 10", and 10'''), a substrate (e.g., shown as 12, 12', 12", and 12'''), and source and drain electrodes or contacts (e.g., shown as 2, 2', 2", 2''', 4, 4', 4", and 4'''). As shown, in each of the configurations, the semiconductor component is in contact with the source and drain electrodes, and the gate dielectric component is in contact with the semiconductor component on one side and the gate electrode on an opposite side.

In certain embodiments, OTFT devices can be fabricated with the present enantiomerically enriched mixture on doped silicon substrates, using $SiO_2$ as the dielectric, in top-contact geometries. In particular embodiments, the active semiconductor layer which incorporates the present enantiomerically enriched mixture can be deposited at room temperature or at an elevated temperature. In other embodiments, the active semiconductor layer which incorporates the present enantiomerically enriched mixture can be applied by spin-coating or printing as described herein. For top-contact devices, metallic contacts can be patterned on top of the films using shadow masks.

In certain embodiments, OTFT devices can be fabricated with the present enantiomerically enriched mixture on plastic foils, using polymers as the dielectric, in top-gate bottom-contact geometries. In particular embodiments, the active semiconducting layer which incorporates the present enantiomerically enriched mixture can be deposited at room temperature or at an elevated temperature. In other embodiments, the active semiconducting layer which incorporates the present enantiomerically enriched mixture can be applied by spin-coating or printing as described herein. Gate and source/drain contacts can be made of Au, other metals, or conducting polymers and deposited by vapor-deposition and/or printing.

In various embodiments, a semiconducting component incorporating the present enantiomerically enriched mixture can exhibit n-type semiconducting activity, for example, an electron mobility of $10^4$ $cm^2$/V-sec or greater and/or a current on/off ratio ($I_{on}/I_{off}$) of $10^3$ or greater.

Other articles of manufacture in which the present enantiomerically enriched mixture are useful are photovoltaics or solar cells. The present enantiomerically enriched mixture can exhibit broad optical absorption and/or a tuned redox properties and bulk carrier mobilities. Accordingly, the present enantiomerically enriched mixture described herein can be used, for example, as an n-type semiconductor in a photovoltaic design, which includes an adjacent p-type semiconductor to form a p-n junction. The present enantiomerically enriched mixture can be in the form of a thin film semiconductor, or a composite including the thin film semiconductor deposited on a substrate.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer ($^1$H, 500 MHz; $^{13}$C, 125 MHz). Electrospray mass spectrometry was performed on a Thermo Finnegan model LCQ Advantage mass spectrometer.

EXAMPLE 1

Preparation of N,N'-bis((R)-substituted)-1,7 (or 1,6)-dicyanoperylene-3,4:9,10-bis(dicarboximide) ((R)—PDI-CN$_2$)

A mixture of PDA-Br$_2$ (1.83 g, 3.33 mmol) and an (R)-(–)-amine (formula IIIa, IIIb, or IIIc) (1.05 g, 10.4 mmol) in 1,4-dioxane (30 mL) was stirred in a sealed flask at 165° C. for two hours. Upon cooling to room temperature, the reaction mixture was concentrated under vacuum. The residue was subjected to column chromatography on silica gel using chloroform as the eluent to give N,N'-bis((R)-substituted)-1,7 (or 1,6)-dibromoperylene-3,4:9,10-bis(dicarboximide) ((R)—PDI—Br$_2$) (1.55 g, 65.1%).

A mixture of (R)—PDI—Br$_2$ (0.35 g, 0.49 mmol) and CuCN (0.26 g, 2.9 mmol) in DMF (7 mL) was stirred at 150° C. for 1 hour. Upon cooling to room temperature, the reaction mixture was filtered to collect the insoluble materials, which were washed with methanol thoroughly. This material was purified by column chromatography on silical gel using chloroform (up to chloroform:ethyl acetate=100:1, 100:4 slowly, v/v) as the eluent to give (R)—PDI-CN$_2$ (0.18 g, 61%).

EXAMPLE 2

Preparation of N,N'-bis((S)-substituted)-1,7 (or 1,6)-dicyanoperylene-3,4:9,10-bis(dicarboximide) ((S)—PDI-CN$_2$)

A mixture of PDA-Br$_2$ (12.0 g, 21.8 mmol) and an (S)-(+)-amine (formula IIIa, IIIb, or IIIc) (6.2 mL, 45.8 mmol) in 1,4-dioxane (180 mL) was stirred in a sealed flask at 165° C. for one hour. After cooling to room temperature, the solvent was removed under vacuum. The solid residue was purified by column chromatography with chloroform as the eluent to give N,N'-bis((S)substituted)-1,7 (or 1,6)-dibromoperylene-3,4:9,10-bis(dicarboximide) ((S)—PDI—Br$_2$) (9.52 g, 61.0%).

A mixture of (S)—PDI—Br$_2$ (9.86 g, 13.76 mmol) and CuCN (7.26 g, 81.06 mmol) in DMF (160 mL) was stirred at 150° C. for 1 hour. After cooling to room temperature, the reaction mixture was filtered to collect the insoluble materials, which were washed with methanol thoroughly. This crude product was subjected to column chromatography on silical gel with chloroform (slowly up to chloroform:ethyl acetate=100:4, v/v) as the eluent to give (S)—PDI-CN$_2$ (6.34 g, 75.7%).

EXAMPLE 3

Preparation of racemic N,N'-bis-substituted-1,7 (or 1,6)-dicyanoperylene-3,4:9,10-bis(dicarboximide) (PDI-CN$_2$)

Hydroxylamine hydrochloride (23.2 g, 0.33 mol) was added to a mixture of ketone 1 (16.3 g, 0.16 mol) and methanol (250 mL), followed by addition of sodium acetate (34.2 g, 0.42 mol). This suspension was vigorously stirred and refluxed for 2 hours. After cooling to room temperature, most of the solvents were removed in vacuo and the residue was poured into water (400 mL). This mixture was extracted with Et$_2$O (300 mL×2). The combined organic layers were washed with water, saturated NaHCO$_3$ and brine, dried over Na$_2$SO$_4$, and concentrated on rotary evaporator, leading to ketoxime 2 (17.6 g, 94%), which was used directly for next step without further purification.

A solution of crude ketoxime 2 (17.6 g, 0.15 mol) in dry Et$_2$O (70 mL) was added dropwise to a suspension of LiAlH$_4$ (11.0 g, 0.28 mol) in dry Et$_2$O (110 mL) at 0° C. After addition, the mixture was refluxed for 16 hours, before it was cooled to 0° C. by an ice/water bath. Water (15 mL) was added slowly to the reaction mixture, followed by addition of an aqueous solution of NaOH (15%, 15 mL) and water (15 mL) in sequence. The reaction mixture was filtered, and the filtrate was dried over Na$_2$SO$_4$, and concentrated on rotary evaporator. The residue was distilled to afford the amine 3 as racemates (8.3 g, 54.2%).

A mixture of PDA-Br$_2$ (1.80 g, 3.27 mmol) and amine 3 (racemic) (1.0 g, 9.9 mmol) in 1,4-dioxane (30 mL) was stirred in a sealed flask at 165° C. for 1.5 hours. Upon cooling to room temperature, the reaction mixture was concentrated under vacuum. The residue was subjected to column chromatography on silica gel using chloroform as eluent to give a racemic mixture of N,N'-bis-substituted-1,7 (or 1,6)-dibromoperylene-3,4:9,10-bis(dicarboximide) (PDI—Br$_2$) (1.70 g, 72.6%).

A mixture of racemic PDI—Br$_2$ (0.99 g, 1.39 mmol) and CuCN (0.75 g, 8.37 mmol) in DMF (20 mL) was stirred at 150° C. for 1 hour. Upon cooling to room temperature, the reaction mixture was filtered to collect the insoluble materials, which were washed with methanol thoroughly. This material was purified by column chromatography on silical gel using chloroform (up to chloroform:ethyl acetate=100:1, 100:4, slowly, v/v) as the eluent to give a racemic mixture of N,N'-bis-substituted-1,7 (or 1,6)-dicyanoperylene-3,4:9,10-bis(dicarboximide) (PDI-CN$_2$) (0.74 g, 87.5%).

EXAMPLE 4

Device Fabrication and Measurements

Thin-film transistor (TFT) devices (50-100 μm channel lengths (L) and 1.0-4.0 mm channel widths (W)) were fabricated using the top-gate bottom-contact configuration with various mixtures of stereoisomers of compounds of formula I incorporated as semiconductor films. Semiconductors films were spin-coated from a solution of chlorinated solvents (2-10 mg/mL) on top of Au electrodes/glass substrates. Next, the gate dielectric layer was spin-coated. Examples of gate dielectrics are PMMA, PS, PVA, PTBS and have thicknesses of 300-1500 nm. The device was completed by deposition of the gate contact. All electrical measurements were performed in ambient atmosphere. Data reported below are average values measured from at least three devices tested at different locations on the semiconductor film.

To allow comparison with other organic FETs, mobilities (μ) were calculated by standard field effect transistor equations. In traditional metal-insulator-semiconductor FETs (MISFETs), there is typically a linear and saturated regime in the $I_{DS}$ vs $V_{DS}$ curves at different $V_G$ (where $I_{DS}$ is the source-drain saturation current, $V_{DS}$ is the potential between the source and drain, and $V_G$ is the gate voltage). At large $V_{DS}$, the current saturates and is given by:

$$(I_{DS})_{sat}=(WC_i/2L)\mu(V_G-V_t)^2 \quad (1)$$

where L and W are the device channel length and width, respectively, $C_i$ is the capacitance of the gate dielectric, and $V_t$ is the threshold voltage.

Mobilities (μ) were calculated in the saturation regime by rearranging equation (1):

$$\mu_{sat}=(2I_{DS}L)/[WC_i(V_G-V_t)^2] \quad (2)$$

The threshold voltage ($V_t$) can be estimated as the x intercept of the linear section of the plot of $V_G$ versus $(I_{DS})^{1/2}$.

Table 1 describes different stereoisomeric mixtures of a compound of formula I obtained by mixing (S,S)-enantiomers and (R,R)-enantiomers of I in the molar ratio shown below:

TABLE 1

| Semiconductor Mixture of I | (S,S)-Enantiomer (%) | (R,R)-Enantiomer (%) |
|---|---|---|
| CZH-V-107: | 0 | 100 |
| CZH-V-154A: | 90 | 10 |
| CZH-V-154B | 80 | 20 |
| CZH-V-154C | 70 | 30 |
| CZH-V-154D: | 60 | 40 |
| CZH-V-154E: | 50 | 50 |

Figure 2:
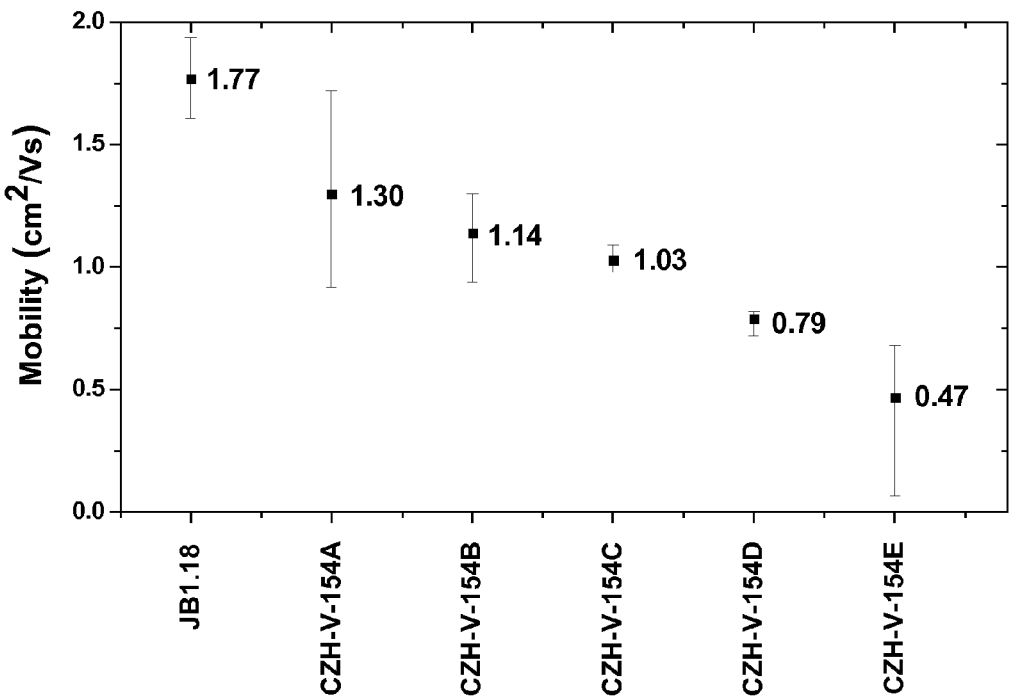
FIG. 2 compares the mobilities of thin film transistors obtained with enantiomerically enriched bis(dicarboximide) mixtures according to the present teachings with those obtained with racemic mixtures and optically pure enantiomers of the bis(dicarboximide). The enantiomerically enriched bis(dicarboximide) mixtures were prepared from stereospecific amines.

FIG. 2 compares the mobilities of TFTs incorporating the different semiconductor mixtures in Table 1.

Table 2 describes different stereoisomeric mixtures of a compound of formula I prepared by cyanating an anhydride of formula II with a mixture of S-amines and R-amines in the molar ratio given below:

TABLE 2

| Semiconductor Mixture of I | S-Amine (%) | R-Amine (%) |
|---|---|---|
| JB1.18 | 100 | 0 |
| CZH-V-107: | 0 | 100 |
| CZH-V-141A | 90 | 10 |
| CZH-V-141B | 70 | 30 |
| CZH-V-93M | 50 | 50 |

Figure 3:
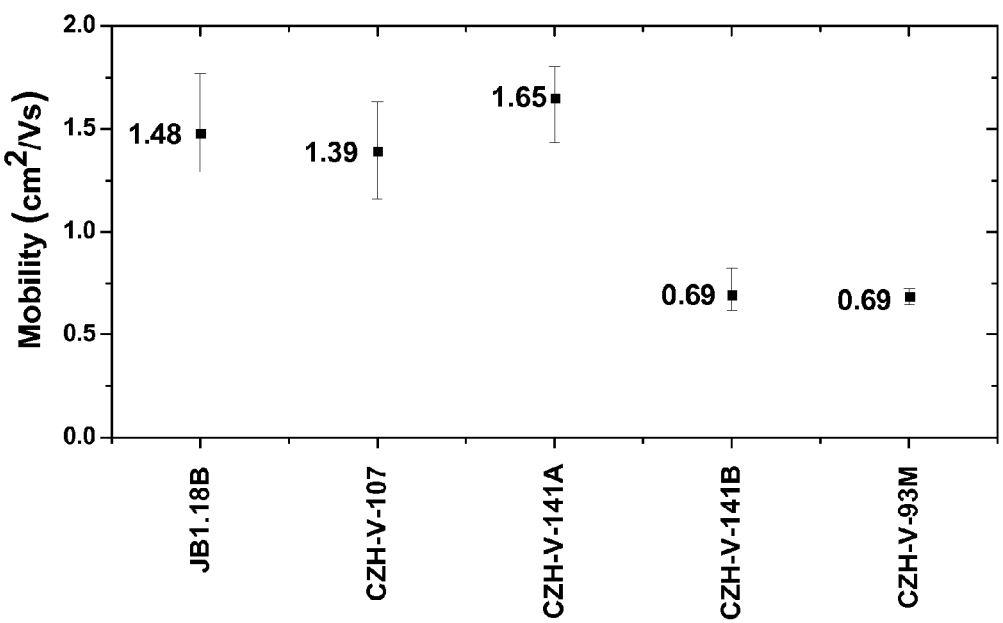
FIG. 3 compares the mobilities of thin film transistors obtained with enantiomerically enriched bis(dicarboximide) mixtures according to the present teachings with those obtained with racemic mixtures and optically pure enantiomers of the bis(dicarboximide). The enantiomerically enriched bis(dicarboximide) mixtures were prepared from enantiomerically enriched amine mixtures.

FIG. 3 compares the mobilities of TFTs incorporating the different semiconductor mixtures in Table 2.

Referring to FIGS. 2 and 3, it can be seen that an enantiomerically enriched mixture according to the present teachings, where (R,R)-stereoisomers:(S,S)-stereoisomers (or vice versa) is between about 0.8:0.2 and about 0.98:0.02 (e.g., CZH-V-154A, CZH-V-154B, or CZH-V-141A), exhibited a mobility that is at least two times higher than the racemate (e.g., CZH-V-154E or CZH-V-93M). In addition, the mobilities measured from these enantiomerically enriched mixtures were not statistically different compared to devices made with optically pure enantiomers (e.g., CZH-V-107 or JB1.18).

The present teachings encompass embodiments in other specific forms without departing from the spirit or essential characteristics thereof. The foregoing embodiments are therefore to be considered in all respects illustrative rather than limiting on the present teachings described herein. The scope of the present teachings is thus indicated by the appended claims rather than by the foregoing description, and all changes that come within the meaning and range of equivalency of the claims are intended to be embraced therein.

The invention claimed is:

1. A thin film semiconductor comprising an enantiomerically enriched mixture of a compound of formula I:

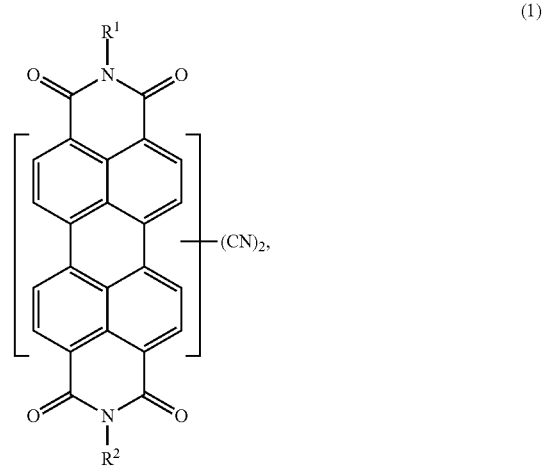

(1)

wherein:

R$^1$ and R$^2$ are identical or substantially identical and are selected from the group consisting of a branched C$_{4-40}$ alkyl group, a branched C$_{4-40}$ alkenyl group, and a branched C$_{4-40}$ haloalkyl group; wherein the branched C$_{4-40}$ alkyl group, the branched C$_{4-40}$ alkenyl group, and the branched C$_{4-40}$ haloalkyl group have a formula selected from the group consisting of:

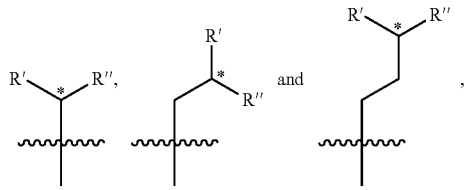

wherein R' is a C$_{1-20}$ alkyl group or a C$_{1-20}$ haloalkyl group; R" is different from R' and is selected from the group consisting of a C$_{1-20}$ alkyl group, a C$_{2-20}$ alkenyl group, and a C$_{1-20}$ haloalkyl group; and an asterisk (*) denotes a stereogenic center such that R$^1$ and R$^2$ have either an R- or S-configuration; and wherein a ratio of (R,R)-stereoisomers:(S,S)-stereoisomers or a ratio of (S,S)-stereoisomers:(R,R)-stereoisomers of the compound of formula I in the enantiomerically enriched mixture is between about 0.8:0.2 and about 0.98:0.02.

2. The thin film semiconductor of claim 1, wherein the enantiomerically enriched mixture comprises two stereoisomers:

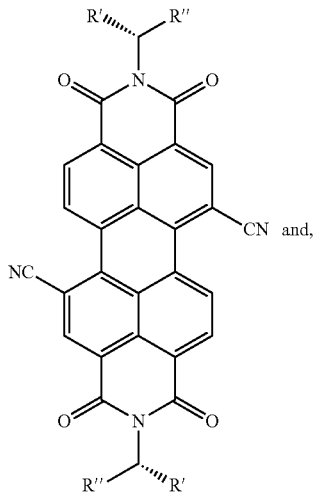

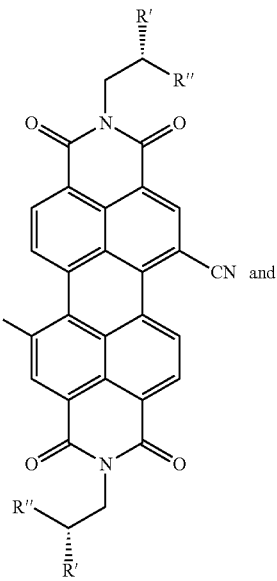

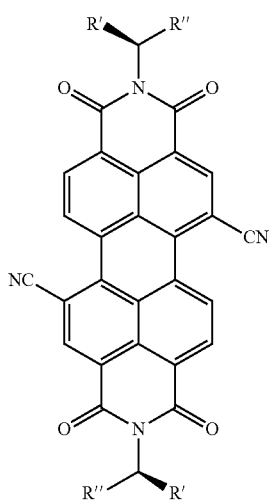

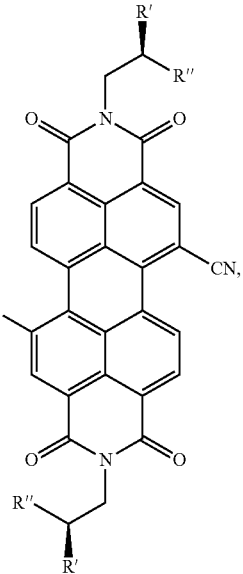

wherein R' is a $C_{1-6}$ alkyl group or a $C_{1-6}$ haloalkyl group; and R" is different from R' and is selected from the group consisting of a $C_{3-20}$ alkyl group, a $C_{3-20}$ alkenyl group, and a $C_{3-20}$ haloalkyl group; and a relative ratio of the two stereoisomers is between about 0.8:0.2 and about 0.98:0.02.

3. The thin film semiconductor of claim 1, wherein the enantiomerically enriched mixture comprises two stereoisomers:

wherein R' is a $C_{1-6}$ alkyl group or a $C_{1-6}$ haloalkyl group; and R" is different from R' and is selected from the group consisting of a $C_{3-20}$ alkyl group, a $C_{3-20}$ alkenyl group, and a $C_{3-20}$ haloalkyl group; and a relative ratio of the two stereoisomers is between about 0.8:0.2 and about 0.98:0.02.

4. The thin film semiconductor of claim 1, wherein the enantiomerically enriched mixture comprises two stereoisomers:

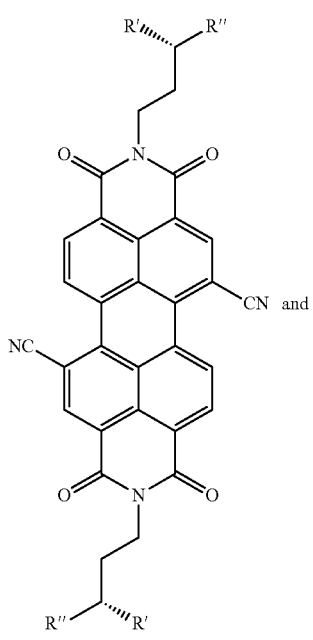

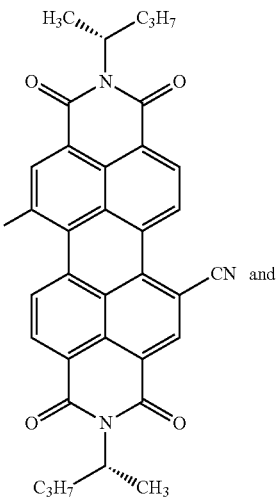

6. The thin film semiconductor of claim 1, wherein the enantiomerically enriched mixture comprises two stereoisomers:

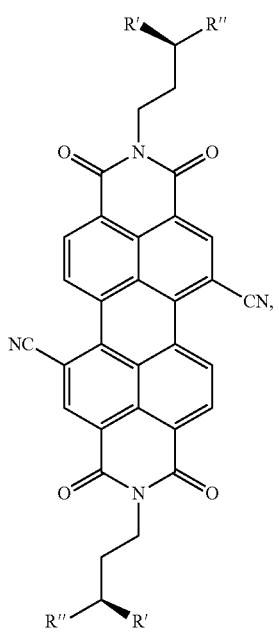

wherein R' is a $C_{1-6}$ alkyl group or a $C_{1-6}$ haloalkyl group; and R" is different from R' and is selected from the group consisting of a $C_{3-20}$ alkyl group, a $C_{3-20}$ alkenyl group, and a $C_{3-20}$ haloalkyl group; and a relative ratio of the two stereoisomers is between about 0.8:0.2 and about 0.98:0.02.

5. The thin film semiconductor of claim 2, wherein R' is selected from the group consisting of $CH_3$, $CF_3$, $C_2H_5$, $CH_2CF_3$, and $C_2F_5$.

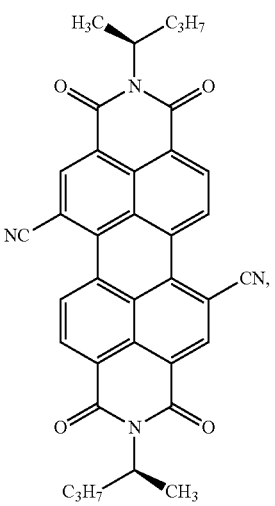

wherein a relative ratio of the two stereoisomers is between about 0.8:0.2 and about 0.98:0.02.

7. The thin film semiconductor of claim 1, wherein the enantiomerically enriched mixture comprises two stereoisomers:

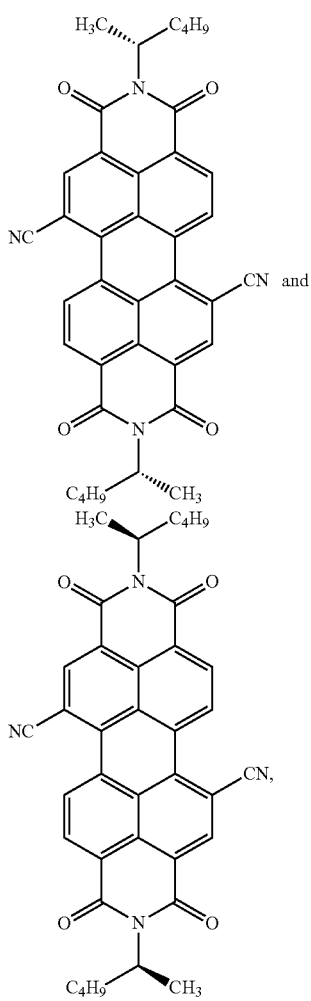

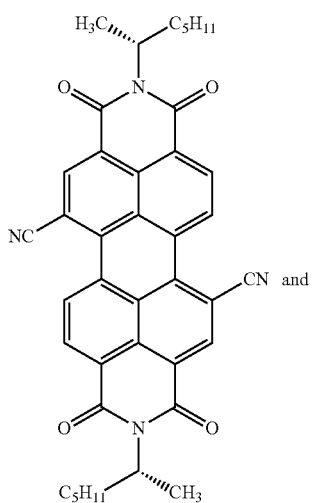

wherein a relative ratio of the two stereoisomers is between about 0.8:0.2 and about 0.98:0.02.

8. The thin film semiconductor of claim 1, wherein the enantiomerically enriched mixture comprises two stereoisomers:

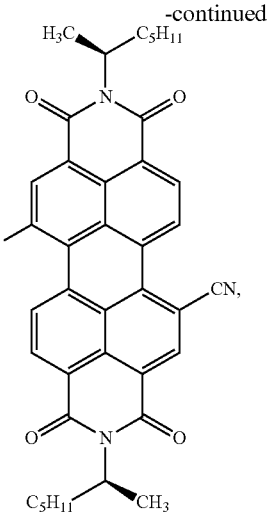

wherein a relative ratio of the two stereoisomers is between about 0.8:0.2 and about 0.98:0.02.

9. The thin film semiconductor of claim 1, wherein the enantiomerically enriched mixture comprises two stereoisomers:

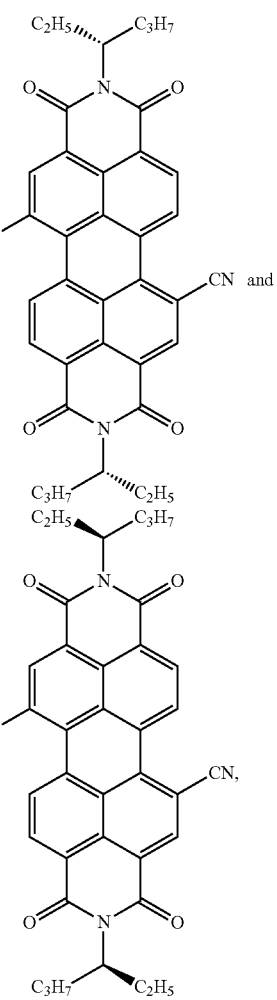

wherein a relative ratio of the two stereoisomers is between about 0.8:0.2 and about 0.98:0.02.

10. The thin film semiconductor of claim 1, wherein the enantiomerically enriched mixture comprises two stereoisomers:

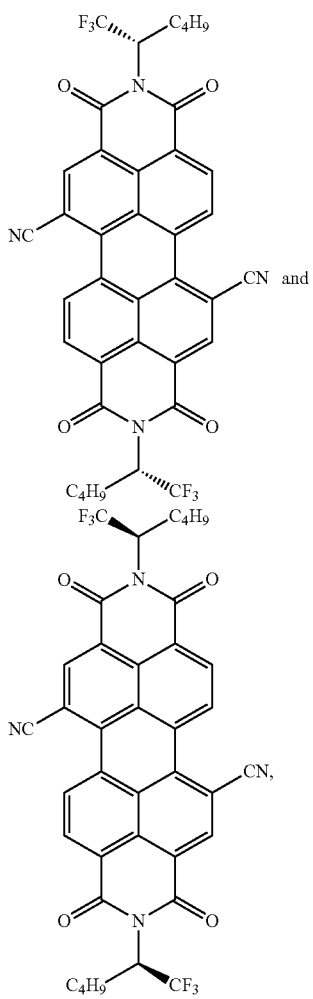

wherein a relative ratio of the two stereoisomers is between about 0.8:0.2 and about 0.98:0.02.

11. The thin film semiconductor of any one of claim 1, wherein the ratio of (R,R)-stereoisomers:(S,S)-stereoisomers or the ratio of (S,S)- stereoisomers: (R,R)-stereoisomers is between about 0.90:0.10 and about 95:0.05.

12. A composite comprising a substrate and the thin film semiconductor of claim 1 deposited on the substrate.

13. An electronic device, an optical device, or an optoelectronic device comprising the thin film semiconductor of claim 1.

14. An electronic device, an optical device, or an optoelectronic device comprising the composite of claim 12.

15. A field effect transistor device comprising a source electrode, a drain electrode, a gate electrode, and the thin film semiconductor of claim 1 in contact with a dielectric material.

16. The field effect transistor device of claim 15, wherein the field effect transistor has a structure selected from the group consisting of a top-gate bottom-contact structure, a bottom-gate top-contact structure, a top-gate top-contact structure, and a bottom-gate bottom-contact structure.

17. The field effect transistor device of claim 15, wherein the dielectric material comprises an organic dielectric material, an inorganic dielectric material, or a hybrid organic/inorganic dielectric material.

18. The field effect transistor device of claim 15, wherein the field effect transistor device exhibits a field effect mobility that is at least twice as high as an otherwise identical field effect transistor device comprising a thin film semiconductor comprising a 1:1 mixture of the (R,R)-stereoisomers and the (S,S)-stereoisomers of the compound of formula I.

19. The thin film semiconductor of claim 3, wherein R' is selected from the group consisting of $CH_3$, $CF_3$, $C_2H_5$, $CH_2CF_3$, and $C_2F_5$.

20. The thin film semiconductor of claim 4, wherein R' is selected from the group consisting of $CH_3$, $CF_3$, $C_2H_5$, $CH_2CF_3$, and $C_2F_5$.

* * * * *